United States Patent [19]

Collins et al.

[11] Patent Number: 4,843,065
[45] Date of Patent: Jun. 27, 1989

[54] METHOD OF PRODUCING PRODUCTS FOR USE IN THE TREATMENT OF BACTERIAL AND/OR VIRUS INFECTIONS

[76] Inventors: Robert A. Collins, 22 6th Ave.; Philip F. Weighner, Rte. #1, both of Waukon, Iowa 52172

[21] Appl. No.: 108,937

[22] Filed: Oct. 13, 1987

Related U.S. Application Data

[63] Continuation-in-part of Ser. No. 736,268, May 22, 1985, abandoned, which is a continuation-in-part of Ser. No. 545,000, Oct. 24, 1983, abandoned.

[51] Int. Cl.⁴ ............................................. A61K 39/395
[52] U.S. Cl. ........................................ 514/21; 514/2; 514/8; 530/350; 530/414; 530/418; 530/832; 424/85.8
[58] Field of Search ................. 424/85, 86, 87; 514/2, 514/8, 21; 530/414, 418, 832

[56] References Cited

U.S. PATENT DOCUMENTS

| | | | |
|---|---|---|---|
| 3,128,230 | 4/1964 | Heinbach | 424/87 |
| 3,376,198 | 4/1968 | Petersen et al. | 424/85 |
| 3,646,193 | 2/1972 | Michaelson et al. | 424/85 |
| 3,911,108 | 10/1975 | Singh | 424/86 |
| 3,975,517 | 8/1976 | Wilson | 424/87 |
| 4,051,235 | 9/1977 | Plymate | 424/85 |
| 4,377,569 | 3/1983 | Plymate | 424/87 |
| 4,402,938 | 9/1983 | Collins et al. | 424/85 |

Primary Examiner—Lester L. Lee
Assistant Examiner—Jeff P. Kushan
Attorney, Agent, or Firm—Ira Milton Jones

[57] ABSTRACT

A method of preparing remedies for the treatment of bacterial and viral infections which involves introduction into the udder of an ungulate during lactation, a specific vaccine comprising bacterial and/or viral organisms in an inactive state, and the preparation of small dosages of the secretary fluid subsequently withdrawn during lactation from the ungulate thus treated.

4 Claims, No Drawings

METHOD OF PRODUCING PRODUCTS FOR USE IN THE TREATMENT OF BACTERIAL AND/OR VIRUS INFECTIONS

This application is a continuation-in-part of the application of Robert A. Collins et al. Ser. No. 736,268, filed May 22, 1985, itself a continuation-in-part of Ser. No. 545,000, filed Oct. 24, 1983, both now abandoned, and is also related to U.S. Pat. No. 3,376,198 and U.S. Pat. No. 4,402,938, issued Sept. 5, 1983.

The aforesaid copending application concerns the process of producing a homeopathic product which involves the preparation of a homeopathic mother from a selected raw material having either toxic of non-toxic characteristics and the conversion of said mother into a sarcode suitable for use as a homeopathic remedy.

U.S. Pat. No. 4,402,938 concerns a new and useful food factor for use as a nutritional supplement for animals involving introduction into the udder of an ungulate an antigen-like material which can comprise bacteria and/or virus in an active state.

U.S. Pat. No. 3,376,198 to Petersen et al. mentions Porter's suggestion of "manufacturing antibodies in the cow's udder by infusion of antigen into the udder of a lactating cow". The product produced by the method of applicants' invention which was shipped to Lobund for the Herpes tests, had the globulin (antibody carrying molecule) removed by ultra-filtration. The suggested product of Porter, the increase of antibody, is not the product of this invention. Applicants' invention is the production of a remedial product, consisting of the molecules remaining in the whey after all globulin, as well as all other large molecules, are removed by filtration.

The product of this invention does not meet the definition of an antibody by any test, such as agglutination, electrophoresis, or gel diffusions. The product of this invention cannot be tested in vitro by any known biological tests available today, as opposed to the test for the product of Petersen et al. which is an in vitro antibody test.

The present invention, however, primarily concerns the production of a remedial product for use in the treatment of any bacterial and/or viral infection by a process involving introduction into the udder of an ungulate during lactation, a specific vaccine comprising killed organisms prepared from the infection to be treated, and the preparation of the dosages of from 1 to 5cc of the lacteal secretory fluid subsequently withdrawn from the ungulate thus treated.

The Petersen et al. patent is related to the present application in that it concerns the production of antibodies in milk by a process involving introduction of a specific antigen into the udder of an ungulate at spaced intervals during its pre-parturition period, that is, during pregnancy. The main objection to this procedure is that it requires an objectionably long time, up to ninety days, before the ungulate gives birth and the milk containing the desired concentration of antibodies only then becomes available.

In a more specific sense, this application concerns a method of producing a remedial product which can be used to treat viral infections such as Herpes or any other infection including bacterial infections such as leprosy.

In accordance with this invention, applicants introduce into the udder of an ungulate during lactation, a specific vaccine comprising inactive organisms prepared from the infection to be treated. During lactation, lacteal secretory fluid is removed from the ungulate a few days following such treatment and finally small dosages of said lacteal secretory fluid, from 1 to 5 cc, are prepared, following the removal of larger molecules.

Viruses of the simplex Herpes virus (HSV-1) family are widespread and result in many diverse and severe diseases of man. Herpes virus, Varicella-Zoster virus and cytomegalovirus infect most individuals during childhood. Herpes virus type II (HSV II) the causative agent of venereal disease, is less common, but is increasing in incidence at a tremendous and alarming rate, reaching epidemic proportions in the past several years.

After infection, which may be clinical or subclinical, these viruses may establish latent virus infections that may persist for life. HSV-I may result in fever blisters or cold sores, keratitis, or a fatal encephalitis. Cytomegalovirus is the most important environmental cause of congenital birth defects, Varicella Zoster virus causes chickenpox as a primary infection with the recurrent form of the disease expressed as shingles.

In one method of most expeditiously practicing this invention for the production of a remedy for the treatment of Herpes or any other infection of the bacterial or viral type, a vaccine is first prepared from killed bacteria or virus of the disease to be treated. For this purpose a number of vials containing live bacteria or virus (for example eight) of 10 ml each, were heated at a temperature of 60° C., with occasional shaking, for four hours. The contents of the vials were then pooled, and small aliquots were removed for plaque assay in Vero cells to test for heat inactivation. The Herpes passage 4 virus titer was $1.5 \times 10^6$ plaque forming units per ml. No infectious Herpes was detectable by plaque assay after such treatment at 60° C. for four hours.

The Herpes vaccine was infused at four different times into the udder of a selected ungulate at approximately ten-day intervals, at a rate of 5cc per quarter per infusion. The vaccine thus produced was then stored in a frozen state (0° F.) for preservation until used.

In one test, the withdrawal of lacteal fluid from the ungulate thus treated was started three days following the infusion period and was repeated for a period of approximately two weeks. The collected fluid was then pooled and (using methods known to the art, such as centrifugation and precipitation) the fat and casein were removed to produce a whey product. However, for oral administration, it is not necessary to remove the fat or the casein.

Two (five gallon) refrigerated tanks marked 1 and 11 were set up in the lab and piped to a custom-built lab model ultra filter, equipped with a 0.2 micron membrane and a 3-horsepower direct drive pump capable of maintaining 60 psi pressure on the high side of the ultra filter while processing. The inlet on the pump was piped to the outlet of Tank 1. The piping was arranged so that the concentrate from the filter would be returned to the top of Tank 1 and the filtrate would be collected in Tank 11.

A preservative was prepared as follows:
11.25 gm methyl paraben
3.75 gm propyl paraben
2.46 gm NaOH pellets
and was placed in a 500 ml erlenmeyer flask. Hot distilled water was added while swirling until all were dissolved. Approximately 100 ml distilled water was used.

Ten liters of the whey product processed above was put into the refrigerated Tank 1. The 100 ml preservative produced as described above, was added to the whey product in Tank 1 while stirring to obtain a homogeneous solution.

The ultra filter was started and run for two hours. The refrigerated tanks kept the temperature below 100° F. The filtrate collected in Tank II was then filtered using a Seitz filter equipped with a 0.02 micron filter. From this point on, all work was done in a sterile room equipped with a high efficiency air filter system. This product was then sterile-filtered by passing through an inline sterile filter equipped with a sterilizing filter cartridge.

The final sterile product was then bottled in sterile 20 ml ampules, that were sealed using a double flame ampule sealer. Ten percent (10%) of the vials were then tested for sterility.

Small dosages, for example 1 to 5 cc of the resulting product can be used in either the liquid form, diluted or undiluted, or in a dried state when encapsulated. Drying can be readily accomplished by freezing.

A product made earlier in the same way, except that infusion of the vaccine was performed pre-partum, was tested on mice at the Lobune Institute of the University of Notre Dame. Those tests revealed that there was a statistically significant decrease in the death rate of mice protected by the lacteal secretion of Herpes infused cows when challenged with a lethal dose of Herpes virus. Tests made thus far on the product produced by infusion during lactation indicate that the same efficacy of the product can be achieved in as little as three days following the infusion period.

Further testing of this latter product is currently being done at the laboratories of D & S Associates in Madison, Wis.

The term "small dosages" as used herein and in the claims can be defined as quantities as small as 1.0 ml to 0.5 ml, or up to 1 to 5 cc. Of significance is the fact disclosed by this earlier testing that, in some instances, the smaller (0.5 ml) dosages were more effective than the larger dosages. However, doses even smaller than 0.5 ml also have been found to be effective. In the earlier test cases it was found that "a large statistically significant increase in resistance to HSV-1" was achieved in mice challenged with that virus after injection of 1.0 ml per day of the product produced by the instant method, over a period of eight days.

A product suitable for use in the treatment of bacterial infections can be produced in the same way as described herein, except that the vaccine introduced during lactation into the udder of the selected ungulate is prepared from the bacterial infection to be treated. Again, in this case, the active organisms in the bacteria are killed to render the vaccine completely inactive.

From the foregoing description, it will be apparent to those skilled in the art that the remedial product of this invention provides an effective treatment for viral and bacterial infections for which there was heretofore no known remedy.

The invention is defined by the following claims:

We claim:

1. The method of producing a remedial product useful in the treatment of bacterial and/or viral infections consisting essentially of:

A. preparing a vaccine of killed microorganisms of the infection to be treated;

B. during lactation, introducing into the udder of an ungulate by infusion or injection, the vaccine comprising killed microorganisms prepared from those of the infection to be treated;

C. removing lacteal secretory fluid in about two days from the ungulate thus treated;

D. filtering out larger molecules including antibodies from the lacteal secretory fluid with approximately a 0.2 micro filter; and E. preparing dosages of the remaining lacteal secretory fluid proportional in amount to the size of the animal to be treated.

2. The method of claim 1 further comprising the removal of fat from said lacteal secretory fluid prior to preparation of said dosages.

3. The method of claim 2 further comprising the removal of casein from said lacteal secretory fluid prior to preparation of said dosages.

4. The method of producing a remedial product useful in the treatment of bacterial and/or viral infections consisting essentially of:

A. during lactation, introducing into the udder of an ungulate a vaccine comprising killed microorganisms prepared from those of the infection to be treated;

B. removing lacteal secretory fluid from the ungulate thus treated in about two days after introduction into the udder;

C. filtering out larger molecules including antibodies from the lacteal secretory fluid with approximately a 2 micron filter and pressurizing fluid on the inlet side;

D. preparing approximately 1 to 5 cc dosages of the filtered fluid.

* * * * *